United States Patent [19]

Burckhardt

[11] Patent Number: 4,584,314

[45] Date of Patent: Apr. 22, 1986

[54] LACTONE DERIVATIVE, PROCESS FOR THE PREPARATION THEREOF, AND USE THEREOF IN PEST CONTROL

[75] Inventor: Urs Burckhardt, Basel, Switzerland

[73] Assignee: Ciba-Geigy Corporation, Ardsley, N.Y.

[21] Appl. No.: 672,029

[22] Filed: Nov. 16, 1984

[30] Foreign Application Priority Data

Nov. 25, 1983 [CH] Switzerland ........................ 6323/83
May 28, 1984 [CH] Switzerland ........................ 2610/84

[51] Int. Cl.$^4$ .................. C07D 495/20; C07D 495/22; A01N 43/22; A61K 31/365
[52] U.S. Cl. .................................... 514/450; 549/264; 549/265
[58] Field of Search ................. 549/264, 265; 536/6.5, 536/7.1, 7.2; 514/450

[56] References Cited

U.S. PATENT DOCUMENTS 3,950,360 4/1976 Aoki et al. ............................ 549/264
4,156,720 5/1979 Fisher et al. ........................ 536/7.1

OTHER PUBLICATIONS

Hedge et al., Tetrahedron Letters, vol. 21, pp. 441-444, (1980), "The Reaction of Hypochlorous Acid with Olefins, Convenient Synthesis . . . ".
Hedge et al., Tetrahedron Letters, vol. 22, pp. 5019-5022, No. 5, (1981), "Hypochlorous Acid, Reaction with Conjugated Ketones . . . ".

Primary Examiner—Glennon H. Hollrah
Assistant Examiner—Dara Dinner
Attorney, Agent, or Firm—Edward McC. Roberts

[57] ABSTRACT

The compound of formula I

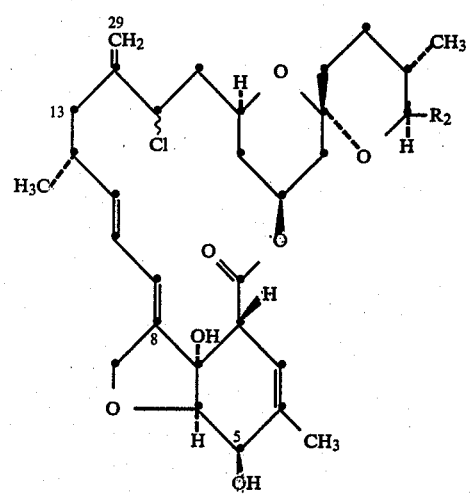

wherein $R_2$ is methyl, ethyl, isopropyl or sec-butyl, can be prepared by selective chlorination of an appropriate milbemycin derivative either with hypochlorous acid (HOCl) or sulfuryl chloride ($SO_2Cl_2$) in the temperature range from $-10°$ to $+60°$ C. It is employed as pesticide for controlling Arthropode species such as injurious insects or ecto- or endoparasites of animals, and is applied in the form of compositions. This compound is also used as intermediate for obtaining further milbemycin derivatives.

5 Claims, No Drawings

LACTONE DERIVATIVE, PROCESS FOR THE PREPARATION THEREOF, AND USE THEREOF IN PEST CONTROL

The present invention relates to a milbemycin derivative of the formula I and to the preparation thereof. The invention further relates to the use of the novel compound as intermediate for obtaining further derivatives of milbemycin macrolides, to the use thereof for controlling pests, and to pesticidal compositions which contain the novel compound as active ingredient.

Specifically, the invention relates to the milbemycin derivative of the formula I

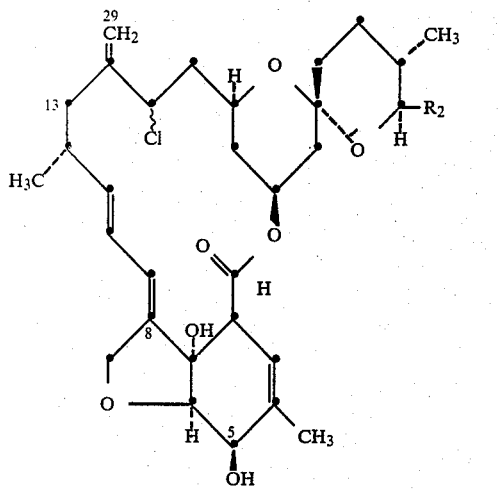

wherein $R_2$ is methyl, ethyl, isopropyl or sec-butyl.

The compound of formula I is prepared by selectively chlorinating a milbemycin derivative of the formula II in the temperature range from $-10°$ to $+60°$ C., preferably from $0°$ to $40°$ C., in the presence of a solvent, in accordance with the following reaction scheme:

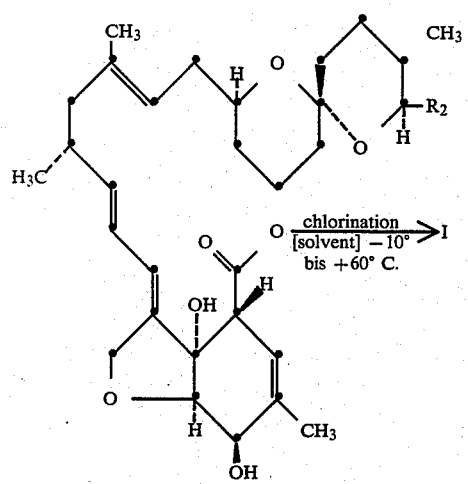

$R_2 = CH_3$ milbemycin $A_3$ from U.S. Pat. No. 3,950,360

$R_2 = C_2H_5$ milbemycin $A_4$ from U.S. Pat. No. 3,950,360

$R_2 = isoC_3H_7$ milbemycin D from U.S. Pat. No. 4,346,171

$R_2 = sec$-$C_4H_9$ 13-deoxy-22,23-dihydro-C-076-Bla-aglycon, or 13-deoxy-22,23-dihydro-avermectin-Bla-aglycon from U.S. Pat. No. 4,173,571.

The above reaction takes the form of a chlorination in the 15-position with the simultaneous formation of an exocyclic double bond in the 29,14-position. A suitable chlorinating agent for such a selective chlorination at a terminal trisubstituted double bond, as represented by the methylalkene grouping in milbemycin, and especially where hydroxyl groups are simultaneously present in the molecule, is hypochlorous acid (HOCl) [Sh. G. Hedge et al., Tetrahedron Letters 21, pp. 441–444 (1980)]. As a rule, HOCl is used in the form of an aqueous solution of an alkali hypochlorite or alkaline earth hypochlorite and the HOCl is liberated with a weak acid.

It is a further aspect of the invention that sulfuryl chloride ($SO_2Cl_2$) can be used instead of HOCl for the chlorination reaction.

Suitable reaction media are inert solvents or mixtures thereof, for example aliphatic or aromatic hydrocarbons, preferably halogenated hydrocarbons, such as benzene, toluene, chlorobenzene, carbon tetrachloride, chloroform, dichloromethane; ethers or ethereal compounds such as diethyl ether, dioxan, tetrahydrofuran; nitriles such as acetonitrile; and water. The preferred solvent is dichloromethane.

The reaction can be carried out in homogeneous or heterogeneous phase (e.g. dichloromethane/water) and in both cases gives surprisingly high yields.

The compound of formula I is a versatile intermediate for obtaining further milbemycin derivatives, with the 5-OH group advantageously being protected. Suitable protecting groups are acyl radicals (such as acetyl, propionyl, benzoyl, methanesulfonyl, tolylsulfonyl and the like) and, in particular, silyl groups. Possible silyl groups are in particular: trimethylsilyl, methyldiphenylsilyl, tris(tert-butyl)silyl, diphenyl-tert-butylsilyl, bis-(isopropyl)methylsilyl and tert-butyldimethylsilyl. The 5-OH group can also be in the form of benzyl ether or methoxyethoxymethyl ether.

The compound of formula I is suitable for controlling pests of animals and plants, including ectoparasites and endoparasites of animals. These last mentioned pests comprise those of the order Acarina, in particular pests of the families Ixodidae, Dermanyssidae, Sarcoptidae, Psoroptidae; of the orders Mallophaga, Siphonoptera, Anoptera (e.g. family of the Haematopinidae); and of the order Diptera, in particular pests of the families Muscidae, Calliphoridae, Oestrididae, Tabanidae, Hippoboscidae, and Gastrophilidae.

The compound of formula I can also be used against hygiene pests, especially of the order Diptera (families Sarcophigiae, Anophilidae and Culicidae); of the order Orthoptera (e.g. family of the Blattidae), and of the order Hymenoptera (e.g. family of the Formicidae).

The compound of formula I also has a lasting action against mites and insects which are parasites of plants. When used to control spider mites of the order Acarina, they are effective against eggs, nymphs and adults of Tetranychidae (Tetranychus spp. and Panonychus spp. It also has excellent activity against sucking insects of the order Homoptera, in particular against pests of the families Aphididae, Delphacidae, Cicadellidae, Psyllidae, Loccidae, Diaspididae and Eriophyidae (e.g. the rust mite on citrus fruit); of the orders Hemiptera, Heteroptera and Thysanoptera; and against plant-destructive insects of the orders Lepidoptera, Coleoptera, Diptera and Orthoptera.

The compound of formula I is also suitable for use as soil insecticide against pests in the soil.

The compound of formula I is therefore effective against all development stages of sucking and eating insects in crops such as cereals, cotton, rice, maize, soybeans, potatoes, vegetables, fruit, tobacco, hops, citrus fruit, avocados and others.

The compound of formula I is also effective against plant nematodes of the species Meloidogyne, Heterodera, Pratylenchus, Ditylenchus, Radopholus, Rhizoglyphus and others.

Furthermore, the compound of formula I acts against helminths, among which the endoparasitic nematodes can be the cause of severe diseases in mammals and fowl, for example in sheep, pigs, goats, cattle, horses, donkeys, dogs, cats, guinea pigs, cage-birds. Typical nematodes having this indication are: Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Cappillaria, Heterakis, Toxocara, Ascaridia, Oxyuris, Ancylostoma, Uncinaria, Toxascaris and Parascaris. The particular advantage of the compound of formula I is its activity against those parasites which are resistant to benzimidzole-based endoparasiticides.

Certain species of the genera Nematodirus, Cooperia and Oesophagostomum attack the intestinal tract of the host animal, whereas others of the species Haemonchus and Ostertagia parasiticise in the stomach and those of the species Dictyocaulus in the lung tissue. Parasites of the families Filariidae and Setariidae are found in internal cell tissue and internal organs, e.g. in the heart, blood vessels, lymph vessels and in subcutaneous tissue. The compound of formula I is effective against these parasites.

The compound of formula I is also suitable for controlling pathogenic parasites in humans, among which parasites there may be mentioned as typical representatives occurring in the alimentary tract those of the species Ancylostoma, Necator, Ascaris, Strongyloides, Trichinella, Capillaria, Trichuris and Enterobius. The compound of this invention is also effective against parasites of the species Wucheraria, Brugia, Onchocerca and Loa of the family of the Filariidae which occur in the blood, in tissue and various organs, and, in addition, against Dracunculus and parasites of the species Strongyloides and Trichinella which infest in particular the exointestinal tract.

The compound of formula I is used in unmodified form or, preferably, together with the adjuvants conventionally employed in the art of formulation, and is therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The compound of formula I is administered to warm-blooded animals at rates of application of 0.01 to 50 mg/kg of body weight, and is applied to enclosed crop areas, to pens, livestock buildings or other buildings in amounts of 10 g to 1000 g per hectare.

The formulations, i.e. the compositions or preparations containing the compound (active ingredient) of the formula I are prepared in known manner, e.g. by homogeneously mixing and/or grinding the active ingredient with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl and monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

The surfactants customarily employed in the art of formulation are described e.g. in "McCutcheon's Detergents and Emulsifiers Annual", MC Publishing Corp. Ridgewood, N.J., 1982.

The pesticidal compositions usually contain 0.01 to 95%, preferably 0.1 to 80%, of a compound of the formula I, 5 to 99.99% of a solid or liquid adjuvant, and 0 to 25%, preferably 0.1 to 25%, of a surfactant.

Whereas commercial products are preferably formulated as concentrates, the end user will normally employ dilute formulations having a concentration of 1-10,000 ppm.

Accordingly, the present invention further relates to pesticidal compositions which contain, as at least one active ingredient, a compound of formula I, together with conventional carriers and/or diluents.

The compositions may also contain further ingredients, such as stabilisers, antifoams, viscosity regulators, binders, tackifiers as well as fertilisers or other active ingredients in order to obtain special effects.

PREPARATORY EXAMPLES

EXAMPLE P1

$\Delta^{29,14}$-15H-15-chloromilbemycin D 2.23 g (4 mM) of milbemycin D are dissolved at room temperature in 100 ml of analytically pure dichloromethane and to this solution is added a solution of 820 mg (8 mM) of Ca(OCl)$_2$ (about 70%) in 10 ml of distilled water. With efficient stirring, small pieces of solid CO$_2$ are added to the resultant suspension from time to time in order to liberate the hypochlorous acid, which amounts in all to about three times the stoichiometrically required amount. The phases are separated and the organic phase is dried over Na$_2$SO$_4$, filtered, and concentrated, affording 2.3 g (85% of theory) of compound I with a melting point of 137°-140° C. (decomp.).

EXAMPLE P2

Preparation of the same compound 4.45 g (8 mM) of milbemycin D are dissolved in 100 ml of analytically pure dichloromethane and then 0.65 ml (16 mM) of sulfuryl chloride are gently stirred in at room temperature. The clear, colourless solution is stirred for 15 hours at about 25° C., then washed three times with a saturated aqueous solution of NaHCO$_3$ and once with water. The aqueous phase is separated and the organic phase is dried over Na$_2$SO$_4$, filtered and concentrated, affording 4.8 g of compound I as an amorphous solid which is purified by flash chromatography. Yield: 2 g of compound I (42% of theory) with a melting point of 139°-140° C. (decomp.).

EXAMPLE P3

$\Delta^{29,14}$-15H-15-chloromilbemycin A$_3$ 1.06 g (2 mM) of milbemycin A$_3$ are dissolved in 50 ml of analytically pure dichloromethane and to this solution is added a solution of 410 mg (4 mM) of Ca-(OCl)$_2$ (about 70%) in 5 ml of distilled water. With efficient stirring, small pieces of solid CO$_2$ are added to the resultant suspension from time to time in order to liberate the hypochlorous acid, which amounts in all to about three times the stoichiometrically required amount. The reaction is complete after 2½ to 3 hours. The phases are separated and the organic phase is dried over Na$_2$SO$_4$, filtered and concentrated, affording a residue which is purified by flash chromatography (eluant: 1000:3 mixture of CH$_2$Cl$_2$/methanol). Yield: 250 mg (22% of theory) of the desired A$_3$ derivative. Molecular weight: 563.13; mass spectrum m/e: 562(M+), 434, 312, 181, 151.

EXAMPLE P4

$\Delta^{29,14}$-15H-15-chloromilbemycin A$_4$ 1.08 g (2 mM) of milbemycin A$_4$ are dissolved in 50 ml of analytically pure dichloromethane and to this solution is added a solution of 410 mg (4 mM) of Ca-(OCl)$_2$ (about 70%) in 5 ml of distilled water. With efficient stirring, small pieces of solid CO$_2$ are added to the resultant suspension from time to time in order to liberate the hypochlorous acid, which amounts in all to about three times the stoichiometrically required amount. The reaction is complete after 2½ to 3 hours. The phases are separated and the organic phase is dried over Na$_2$SO$_4$, filtered and evaporated to dryness. The residue is purified by flash chromatography (eluant: dichloromethane), affording 460 mg (39.8% of theory) of the desired A$_4$ derivative. Molecular weight 577.16; mass spectrum m/e: 576 (M+) 448, 312, 195, 167, 151.

EXAMPLE P5

13-deoxy-$\Delta^{29,14}$-15H-15-chloro-22,23-dihydroavermectin-Bla-aglycon

Following the procedure of Example 1 or 2, 119 mg of 13-deoxy-$\Delta^{29,14}$-15H-15-chloro-22,23-dihydro-avermectin-Bla-aglycon can be obtained from 228 mg (0.4 mM) of 13-deoxy-22,23-dihydro-avermectin-Bla-aglycon.

Formulation examples for active ingredients of the formula I (throughout, percentages are by weight)

| Wettable powders | a | b | c |
| --- | --- | --- | --- |
| compound of formula I | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
| --- | --- |
| compound of formula I | 10% |
| octylphenol polyethylene glycol ether (4-5 moles of ethylene oxide) | 3% |
| calcium dodecylbenzenesulfonate | 3% |
| castor oil polygycol ether (36 moles of ethylene oxide) | 4% |
| cyclohexanone | 30% |
| xylene mixture | 50% |

Emulsions of any required concentration can be obtained from this concentrate by dilution with water.

| Dusts | a | b |
| --- | --- | --- |
| compound of formula I | 5% | 8% |
| talcum | 95% | — |
| kaolin | — | 92% |

Ready for use dusts are obtained by mixing the active ingredient with the carriers, and grinding the mixture in a suitable mill.

| Extruder granulate | |
| --- | --- |
| compound of formula I | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

If the compound of formula I, or compositions containing it, are used for controlling endoparasitic nematodes in domestic animals and productive livestock, for example cattle, sheep, goats, horses, pigs, cats and dogs, they can be administered to the animals in both single and repeated doses. Depending on the species of animal, the individual doses are preferably administered in amounts ranging from 0.1 to 10 mg/kg of body weight. A better action is often achieved by protracted administration, or lower total doses will also suffice. The compounds, or compositions containing them, can also be added to feeds and drinks. The ready-prepared feeds contain the active ingredients preferably in a concentration of 0.005 to 0.1 percent by weight. The compositions can be administered to the animals perorally in the form of solutions, emulsions, suspensions, powders, tablets, boluses or capsules.

If the physical and toxicological properties of solutions or emulsions permit it, the compounds of formula I, or compositions containing them, can also be injected into animals, for example subcutaneously or by intraruminal injection, or applied to the bodies of the animals by the pour-on method. Administration by means of salt licks or molasses blocks is also possible.

BIOLOGICAL EXAMPLES

B1: Insecticidal stomach poison action against *Spodoptera littoralis*

Potted cotton plants in the 5-leaf stage are sprayed with a solution containing 3, 12.5 or 50 ppm of the test compound in acetone/water. After the coating has dried, the plants are populated with about 30 larvae ($L_1$ stage) of *Spodoptera littoralis*. Two plants are used for each test compound and test species. The test is carried out at about 24° C. and 60% relative humidity. Evaluations and intermediate evaluations of dead insects, growth, larvae and feeding damage are made after 24, 48 and 72 hours.

Complete kill was achieved after 24 hours with the compounds of formula I even at a concentration of 3 ppm.

B2: Action against plant destructive acarids: OP-sensitive *Tetranychus urticae*

16 hours before the start of the test, the primary leaves of bean plants (*Phaseolus vulgaris*) are infected with an infested piece of leaf from a mass culture of *Tetranychus urticae*. Upon removal of the piece of leaf, the plants infested with all stages of the mites are sprayed to drip point with a solution containing 0.4 ppm or 1.6 ppm of the test compound. The temperature in the greenhouse compartment is about 25° C.

The percentage of mobile stages (adults and nymphs) and of eggs is made under a stereoscopic microscope after 7 days.

The compounds of formula I effected complete kill even at a concentration of 0.4 ppm.

B3: Action against $L_1$ larvae of *Lucilia sericata*

1 ml of an aqueous suspension of test compound is mixed with 3 ml of a special larval culture medium at about 50° C. such that a homogeneous composition containing 250 ppm or 125 ppm is obtained. About 30 *Lucillia sericata* larvae ($L_1$) are put into each test tube containing active ingredient. A mortality count is made after 4 days. The compounds of formula I effected 100% kill at a concentration of 250 ppm.

B4: Acaricidal action against *Boophilus microplus* (Biarra strain)

Adhesive tape is applied vertically across a PVC plate so that 10 fully replete female *Boophilus microplus* ticks (Biarra strain) can be affixed thereto with their backs, side by side, in a row. Each tick is injected from an injection needle with 1 μl of a liquid which contains a 1:1 mixture of polyethylene glycol and acetone, in which mixture a specific amount of test compound of 1, 0.1 or 0.01 μg per tick is dissolved. Control ticks are injected with liquid containing no test compound. After this treatment, the ticks are detached from the support and kept in an insectarium at about 28° C. and 80% relative humidity until oviposition has taken place and the larvae have hatched from the eggs of the control ticks.

The activity of the test compound is determined with the $IR_{90}$, i.e. the effective dose is determined at which 9 out of 10 female ticks (90%) even after 30 days lay eggs from which larvae do not emerge. The compounds of formula I effected an $IR_{90}$ of 0.1 μg.

B5: Trial with sheep infected with nematodes (*Haemonchus concortus* and *Trichostrongylus colubriformis*)

The test compound is administered in the form of a suspension with a stomach probe or by intraruminal injection to sheep which have been artificially infected with *Haemonchus concortus* and *Trichostrongylus*. One to three animals are used for each dose. Each sheep is treated only once with a single dose, namely with 1 mg or 2 mg/kg of body weight. Evaluation is made by comparing the number of worm eggs excreted in the faeces of the sheep before and after treatment. Untreated sheep infected simultaneously and in the same manner are used as controls. In comparison with untreated and infected control groups, no nematode infestation (complete reduction of eggs in the faeces) was found in sheep which were treated with one of the compounds of formula I at 2 mg/kg.

B6: Contact action against *Aphis craccivora*

Pea cuttings which have been infested with all development stages of the aphid are sprayed with a solution prepared from an emulsifiable concentrate formulation of the test compound and containing 50, 25 or 12.5 ppm of active ingredient. Evaluation takes place to determine the minimum concentration of a.i. where the mortality of the aphids is more than 80% after 3 days. A composition is only rated as effective at this level of activity.

Complete kill (100%) was achieved with the compounds of formula I at a concentration of 12.5 ppm.

B7: Larvicidal action against *Aedes aegypti*

A 0.1% solution of the test compound in acetone is pipetted onto the surface of 150 ml of water in a beaker in an amount sufficient to give concentrations of 10, 3.3 and 1.6 ppm. After the acetone has evaporated, 30–40 three-day-old larvae of *Aedes aegypti* are put into the beaker containing the test compound. Mortality counts are made after 1, 2 and 5 days.

In this test, the compounds of formula I effected complete kill of all larvae at a concentration of 1.6 ppm after 1 day.

What is claimed is:

1. A milbemycin derivative of the formula I

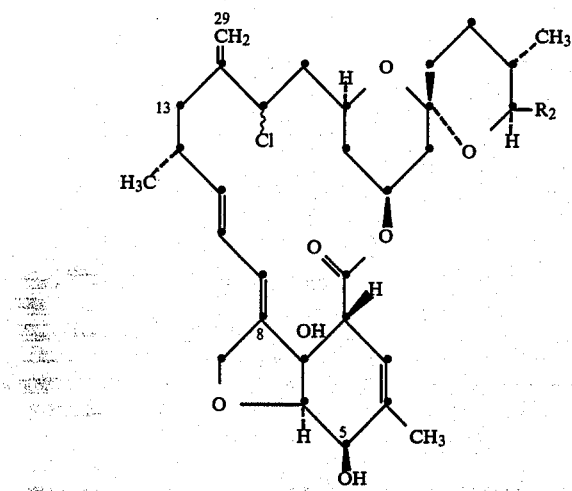

wherein $R_2$ is methyl, ethyl, isopropyl or sec-butyl.

2. A pesticidal composition containing, as at least one active ingredient, an effective amount of the compound of formula I

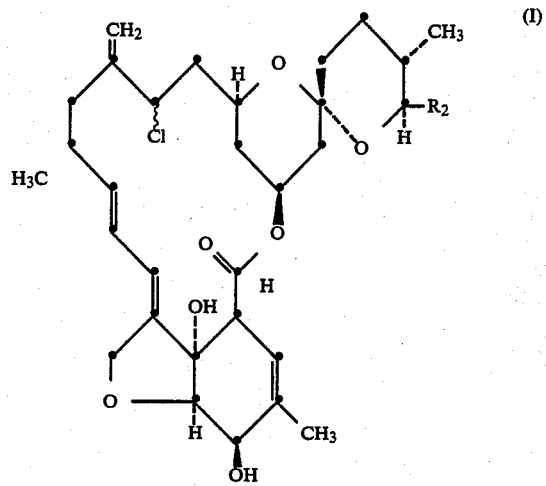

wherein $R_2$ is methyl, ethyl, isopropyl or sec-butyl, together with a suitable inert carrier and/or diluent.

3. A method of controlling insects and representatives of the order Acarina which are plant parasites, which comprises applying to them an effective amount of a compound of formula I according to claim 1.

4. A method of controlling ecto- and endoparasites in warm-blooded animals, which comprises applying to said animals a pesticidally effective amount of a compound of the formula I according to claim 1.

5. A method of controlling endoparasitic nematodes in animals, which method comprises treating said animals with a nematacidally effective amount of a compound of claim 1.

* * * * *